(12) United States Patent
Katayama (10) Patent No.: US 8,480,562 B2
(45) Date of Patent: Jul. 9, 2013

(54) CAPSULE MEDICAL APPARATUS

(75) Inventor: Miho Katayama, Yokohama (JP)

(73) Assignee: Olympus Medical Systems Corp., Tokyo (JP)

(*) Notice: Subject to any disclaimer, the term of this patent is extended or adjusted under 35 U.S.C. 154(b) by 135 days.

(21) Appl. No.: 12/897,955

(22) Filed: Oct. 5, 2010

(65) Prior Publication Data

US 2011/0207998 A1 Aug. 25, 2011

Related U.S. Application Data

(63) Continuation of application No. PCT/JP2010/059140, filed on May 28, 2010.

(30) Foreign Application Priority Data

May 29, 2009 (JP) ................................. 2009-131365

(51) Int. Cl.
*A61B 1/00* (2006.01)
*A61B 1/04* (2006.01)
*A61B 1/06* (2006.01)

(52) U.S. Cl.
USPC ............ 600/107; 600/106; 600/109; 600/160

(58) Field of Classification Search
USPC ................. 600/106, 107, 109, 117, 118, 160, 600/170, 178
See application file for complete search history.

(56) References Cited

U.S. PATENT DOCUMENTS

| | | | |
|---|---|---|---|
| 6,283,947 B1 * | 9/2001 | Mirzaee | 604/264 |
| 6,346,099 B1 * | 2/2002 | Altman | 604/528 |
| 7,066,879 B2 * | 6/2006 | Fowler et al. | 600/102 |
| 7,914,442 B1 * | 3/2011 | Gazdzinski | 600/109 |
| 7,946,979 B2 * | 5/2011 | Gilad et al. | 600/109 |
| 2008/0199065 A1 * | 8/2008 | Swain | 382/133 |
| 2009/0137866 A1 | 5/2009 | Boyden et al. | |

FOREIGN PATENT DOCUMENTS

| | | |
|---|---|---|
| JP | S58-19233 | 2/1983 |
| JP | H04-144533 | 5/1992 |
| JP | 2002-000556 | 1/2002 |
| JP | 2003-325438 | 11/2003 |
| WO | WO 2007/069697 A1 | 6/2007 |

OTHER PUBLICATIONS

International Search Report dated Jun. 29, 2010.
Decision on Patent Grant dated Nov. 9, 2010.

* cited by examiner

*Primary Examiner* — Alireza Nia
(74) *Attorney, Agent, or Firm* — Scully, Scott, Murphy & Presser, P.C.

(57) ABSTRACT

A capsule medical apparatus capable of injecting a medical agent into a living tissue includes a casing, a pressing member that presses the surface of the living tissue, a driving unit that causes the pressing member to protrude from the casing in a predetermined direction and to press the surface of the living tissue while rotating the pressing member around a rotation axis parallel to the protruding direction, and a needle-like puncturing member that is arranged on the pressing member and punctures the living tissue in an oblique direction with respect to the surface of the living tissue to thereby inject the medical agent into the living tissue along with the rotation of the pressing member driven by the driving unit.

9 Claims, 9 Drawing Sheets

CAPSULE MEDICAL APPARATUS

CROSS-REFERENCE TO RELATED APPLICATIONS

This application is a continuation of PCT international application Ser. No. PCT/JP2010/059140 filed on May 28, 2010 which designates the United States, incorporated herein by reference, and which claims the benefit of priority from Japanese Patent Applications No. 2009-131365, filed on May 29, 2009, incorporated herein by reference.

BACKGROUND OF THE INVENTION

1. Field of the Invention

The present invention relates to a capsule medical apparatus that is insertable into a subject and capable of injecting a medical agent into a living tissue inside the subject.

2. Description of the Related Art

In recent years, in the field of an endoscope, capsule-shaped body-insertable apparatuses (e.g., capsule endoscopes) equipped with an imaging function and a radio communication function have been proposed, and body-insertable apparatus systems that capture in-vivo images of a subject by using the capsule endoscopes have been developed. A capsule endoscope is, for example, swallowed by a subject in order to observe (examine) the interior of the subject. Thereafter, the capsule endoscope moves through the body cavity, such as the internal organs including the stomach and the small intestine, by peristalsis of the internal organs and functions to capture in-vivo images of the subject at intervals of, for example, 0.5 second until the capsule endoscope is naturally excreted.

While the capsule endoscope moves through the inside of the subject, an external image display device receives the images captured by the capsule endoscope via antennas arranged on the body surface of the subject. The image display device has a function for communicating with the capsule endoscope by radio and an image memory function, and sequentially stores, in a memory, the images received from the capsule endoscope in the subject. Doctors or nurses can observe (examine) the interior of the subject to make a diagnosis by displaying the images accumulated in the image display device, i.e., the images of the inside of the gastrointestinal tract of the subject, on a display.

Japanese Laid-open Patent Publication No. 2003-325438 discloses a capsule medical apparatus that allows to externally control operations of pulling out, rotating, or opening/closing a manipulator such as a treatment instrument mounted on a capsule main body, at a specific site.

SUMMARY OF THE INVENTION

A capsule medical apparatus according to an aspect of the present invention includes a casing; a pressing member that presses a surface of a living tissue; a driving unit that causes the pressing member to protrude from the casing and to press the surface of the living tissue while rotating the pressing member around a rotation axis parallel to a direction in which the pressing member protrudes; and a needle-like puncturing member that is arranged on the pressing member and punctures the living tissue in an oblique direction with respect to the surface of the living tissue to thereby inject a medical agent into the living tissue along with the rotation of the pressing member driven by the driving unit.

A capsule medical apparatus according to another aspect of the present invention includes a casing; a pressing means for pressing a surface of a living tissue; a driving means for causing the pressing means to protrude from the casing and to press the surface of the living tissue while rotating the pressing means around a rotation axis parallel to a direction in which the pressing means protrudes; and a needle-like puncturing means, arranged on the pressing means, for puncturing the living tissue in an oblique direction with respect to the surface of the living tissue to thereby inject a medical agent into the living tissue along with the rotation of the pressing means driven by the driving means.

The above and other features, advantages and technical and industrial significance of this invention will be better understood by reading the following detailed description of presently preferred embodiments of the invention, when considered in connection with the accompanying drawings.

DETAILED DESCRIPTION OF THE PREFERRED EMBODIMENTS

Exemplary embodiments of a capsule medical apparatus according to the present invention will be explained in detail below with reference to the accompanying drawings. The present invention is not limited by the following embodiments.

Figure 1:
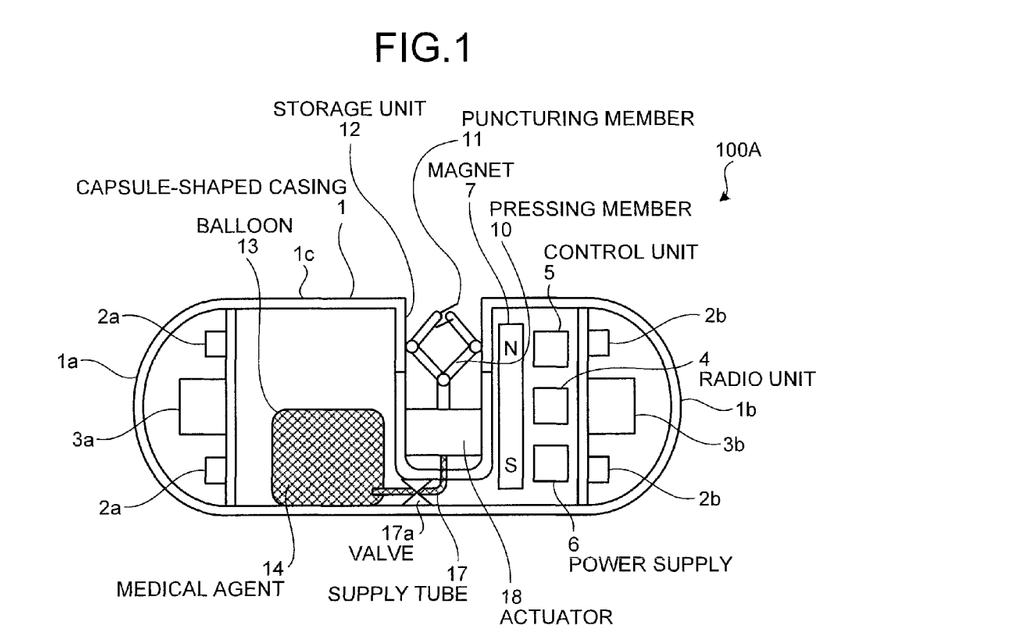
FIG. 1 is a schematic diagram illustrating an internal configuration of a capsule medical apparatus according to an embodiment of the present invention.

FIG. 1 is a schematic diagram illustrating an internal configuration of a capsule medical apparatus according to an embodiment of the present invention. As illustrated in FIG. 1, a capsule medical apparatus 100A is a capsule-shaped medical apparatus formed in a size that allows the capsule medical apparatus to be inserted into a subject. The capsule medical apparatus 100A is introduced into the subject and injects a medical agent into a living tissue such as a cell.

In the capsule medical apparatus 100A, various functional components are housed in a capsule-shaped casing 1, in which both open ends of a cylindrical casing 1c are respectively sealed with transparent dome-shaped casings 1a and 1b and of which interior is kept liquid-tight. Imaging units 3a and 3b, which are formed of an imaging element, a condenser optical system, and the like and capture in-vivo images inside the subject, are arranged on the axis of the capsule-shaped casing 1 and in the vicinity of the dome-shaped casings 1a and 1b. Furthermore, illuminating units 2a and 2b, which are formed of LEDs and the like, are annularly arranged in radially outward directions of the imaging units 3a and 3b, respectively.

A storage unit 12 for storing a pressing member 10 as a pressing means, an actuator 18 as a driving means, and puncturing members 11 as puncturing means is arranged in the cylindrical casing 1c of the capsule-shaped casing 1. The pressing member 10 presses the surface of a desired living tissue. The actuator 18 functions as a driving unit that causes the pressing member 10 to protrude from the capsule-shaped casing 1, particularly from the cylindrical casing 1c, in a predetermined protruding direction, and presses the pressing member 10 against the surface of a living tissue while rotating the pressing member 10 around a rotation axis parallel to the protruding direction. The puncturing members 11 are in the form of a needle and arranged on the pressing member 10. The puncturing members 11 puncture the living tissue in an oblique direction with respect to the surface of the living tissue along with the rotation of the pressing member 10 driven by the actuator 18, and inject a medical agent 14 into the living tissue. The medical agent 14 is stored in a balloon 13, and is supplied to the puncturing members 11 via a supply tube 17 having a valve 17a and a pipeline inside the pressing member 10. By opening the valve 17a, the medical agent 14 is pushed out toward the puncturing members 11 side by the contractile action of the balloon 13.

The capsule medical apparatus 100A includes a magnet 7, a radio unit 4, a control unit 5, and a power supply 6 in the capsule-shaped casing 1. The magnet 7 being a magnetic body is arranged such that the magnetization direction thereof matches the radial direction of the capsule-shaped casing 1, and enables axial rotation or translational movement of the capsule medical apparatus 100A in accordance with the application of an external magnetic field. The radio unit 4 transmits by radio various types of information including in-vivo images captured by the imaging units 3a and 3b to the outside of the subject. The control unit 5 controls processes on various components in the capsule-shaped casing 1. The power supply 6 supplies electric power to the various components in the capsule-shaped casing 1 under the control by the control unit 5.

With reference to FIG. 2 to FIG. 5, a process for injecting a medical agent into a living tissue by the capsule medical apparatus 100A illustrated in FIG. 1 will be explained. The control unit 5 transmits in-vivo images sequentially captured by the imaging units 3a and 3b to the outside of the subject via the radio unit 4. An operator observes the transmitted in-vivo images outside the subject and determines whether the capsule medical apparatus 100A has reached the position of a living tissue to which the medical agent 14 is to be injected. When the capsule medical apparatus 100A has reached the position, a magnetic field is applied from the outside to activate a magnetic switch (not shown), so that the process for injecting the medical agent 14 is started. It is possible to forcibly move the capsule medical apparatus 100A. For example, the capsule medical apparatus 100A may be rotated or moved linearly by generating a rotating magnetic field or a gradient magnetic field from the outside. It is possible to arrange a receiving unit in the capsule medical apparatus 100A and transmit by radio an instruction signal from the outside to start the process for injecting the medical agent 14 into the living tissue. It is also possible to arrange a pH sensor in the capsule medical apparatus 100A or cause the capsule medical apparatus 100A to analyze the in-vivo images captured by the imaging units 3a and 3b in order to detect whether the capsule medical apparatus 100A has almost reached a target site in the body so that the process of injecting the medical agent 14 into the living tissue can autonomously started.

Figure 2:
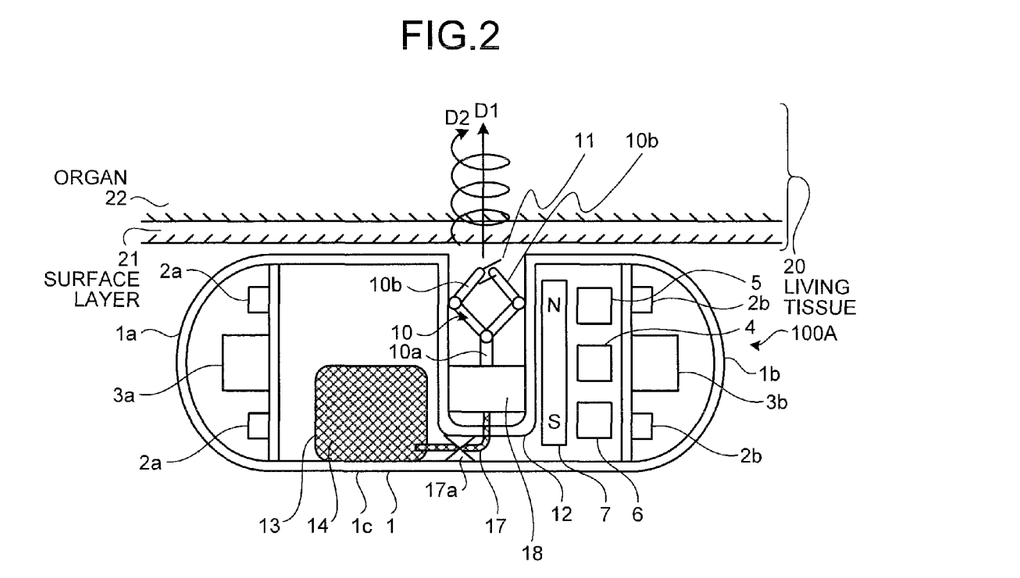
FIG. 2 is a schematic diagram illustrating a state in which the capsule medical apparatus illustrated in FIG. 1 just starts injecting a medical agent into a living tissue.
Figure 3:
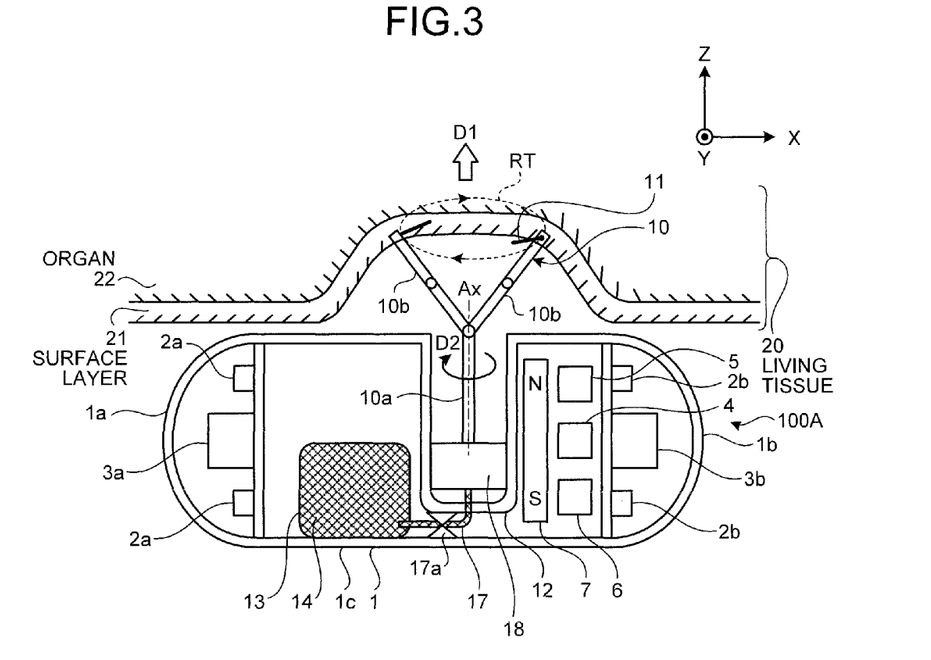
FIG. 3 is a schematic diagram illustrating a state in which the capsule medical apparatus illustrated in FIG. 1 is injecting the medical agent into the living tissue.
Figure 4:
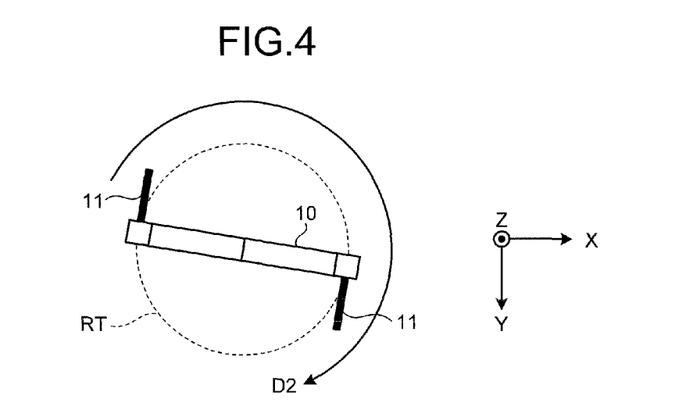
FIG. 4 is a plan view illustrating a positional relationship between a pressing member and puncturing members in the capsule medical apparatus illustrated in FIG. 1.

Once an instruction is issued to start the process for injecting the medical agent into the living tissue, as illustrated in FIG. 2 and FIG. 3, the control unit 5 operates the actuator 18 to cause the pressing member 10 stored in the storage unit 12 to rotate and protrude toward a living tissue 20. In FIG. 2 and FIG. 3, the protruding direction of the pressing member 10 is indicated by arrow D1, the rotation axis of the pressing member 10 is denoted by Ax, and the rotation direction of the pressing member 10 is indicated by arrow D2. The rotation axis Ax extends substantially parallel to the protruding direction of the pressing member 10.

The pressing member 10 is a Y-shaped member, and is stored in the storage unit 12 such that two branch portions 10b and 10b bifurcated from an end of a base portion 10a arranged on the actuator 18 side are folded. When the pressing member 10 protrudes to the outside of the capsule medical apparatus 100A, as illustrated in FIG. 3, each branch portion 10b having been folded is unfolded to thereby form a Y-shape. The Y-shaped pressing member 10 presses the living tissue 20 outside the capsule medical apparatus 100A and is rotated around the axis of the pressing direction (i.e., the protruding direction D1 of the pressing member 10: the same is applied hereinafter) by the actuator 18. That is, the pressing member 10 is rotated about the rotation axis Ax.

The puncturing members 11 in the form of a needle are arranged on respective end portions of the branch portions 10b. When the pressing member 10 is unfolded, particularly when each branch portion 10b is unfolded, each puncturing member 11 is positioned in a plane substantially perpendicular to the rotation axis Ax of the pressing member 10. The puncture direction of each puncturing member 11 corresponds to a direction in which the puncturing member 11 comes into contact with a rotational trajectory RT in the vicinity of the end of the unfolded pressing member 10. More particularly, the puncture direction corresponds to the tangential direction of the rotational trajectory RT (see FIG. 4 and FIG. 5).

Figure 5:
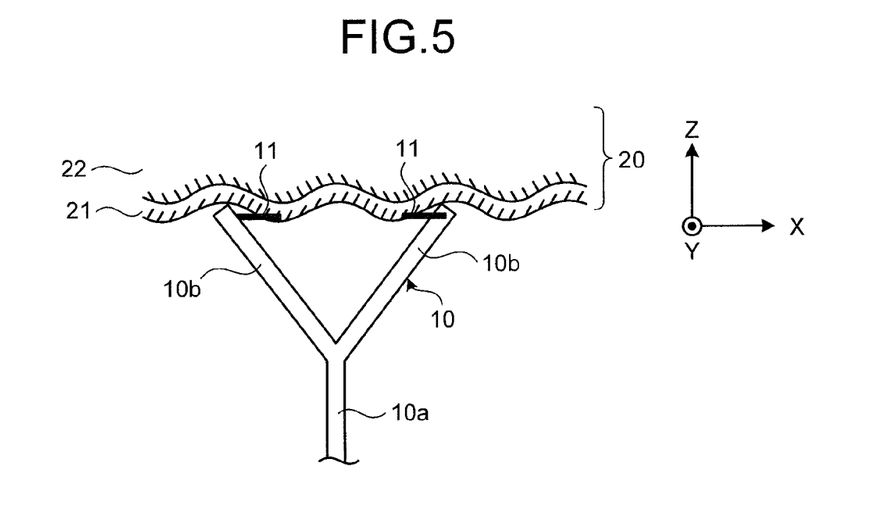
FIG. 5 is a schematic diagram illustrating the positional relationship between the pressing member and the puncturing members in the capsule medical apparatus illustrated in FIG. 1.

As illustrated in FIG. 5, the end portion of the pressing member 10 presses the living tissue 20 and rotates with respect to the surface of the living tissue 20, so that the pressing member 10 twists the surface of the living tissue 20 toward a front side, i.e., toward the base portion 10a side. Therefore, the puncturing members 11 puncture the living tissue 20 in an oblique direction with respect to the surface of the twisted living tissue 20, so that the puncturing members 11 can reliably puncture the living tissue 20. Furthermore, because the puncturing members 11 puncture the living tissue 20 relatively obliquely with respect to the surface of the living tissue 20, discharge ports of the puncturing members 11 can be positioned between a surface layer 21 of the living tissue 20 and an organ 22. In general local injection, it is desirable to administer the medical agent 14 between the surface layer 21 and the organ 22. According to the conventional puncture, puncturing members vertically puncture the living tissue 20, so that the puncture is not easy and is not reliably be performed because of the surface escape or the surface stretching that may occur on the surface of the living tissue 20. Furthermore, because the puncturing members vertically puncture the living tissue 20, it is difficult to control the depth of the puncture, resulting in excessive penetration or the like.

In contrast, according to the embodiment, because the pressing member 10 twists the living tissue 20 and the puncturing members 11 puncture the living tissue 20 relatively obliquely with respect to the surface of the living tissue 20, the puncture can reliably be performed, and the depth of the puncture can easily be controlled to a constant depth.

When the puncturing members 11 puncture the living tissue 20 as described above, load is applied to the rotation of the pressing member 10, so that the rotation of the pressing member 10 is stopped. Then, the control unit 5 performs control so that the valve 17a is opened, the medical agent 14 in the balloon 13 is pushed out toward each puncturing member 11 side, and the medical agent 14 is injected into the living tissue 20 from each puncturing member 11.

Thereafter, the control unit 5 controls the actuator 18 to rotate the pressing member 10 around the rotation axis Ax in a direction opposite to the rotation direction before the medical agent 14 is injected and to move the pressing member 10 away from the living tissue 20. Consequently, each puncturing member 11 is removed from the living tissue 20, and the pressing member 10 is folded and stored in the storage unit 12. Then, the capsule medical apparatus 100A is excreted to the outside of the subject.

It may be possible to only extend the pressing member 10 in the pressing direction without rotation inside the storage unit 12.

Figure 6:
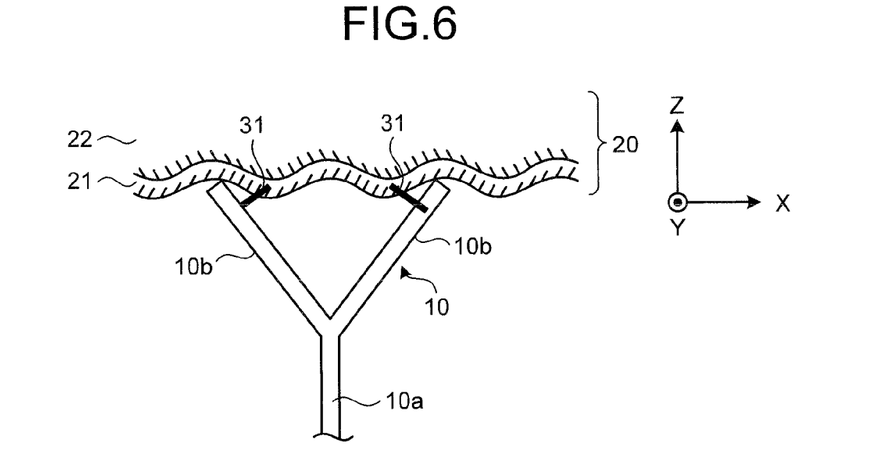
FIG. 6 is a schematic diagram illustrating a modification of a mounting state of the pressing member and the puncturing members in the capsule medical apparatus according to the present invention.

According to the embodiment described above, as illustrated in FIG. 4 and FIG. 5, the puncturing members 11 are arranged in the plane substantially perpendicular to the rotation axis of the pressing member 10 and the puncture direction of the puncturing members 11 is set to coincide with the tangential direction of the rotational trajectory RT of the pressing member 10; however, the present invention is not limited thereto. As illustrated in FIG. 6, puncturing members 31 may be obliquely arranged such that a base portion of each puncturing member 31 is at a position shifted by a predetermined distance from the end of the pressing member 10 toward a base end side of the pressing member 10, and an end of each puncturing member 31 is at a more forward position than the base portion of each puncturing member 31 in the pressing direction of the pressing member 10 when the pressing member 10 protrudes. Accordingly, the puncturing members 31 can reliably puncture the surface of the living tissue 20 at the ends thereof in an oblique manner. Furthermore, a force applied to the puncturing members 31 by the living tissue 20 can be distributed toward the pressing member 10 side, so that it is possible to prevent the puncturing members 31 from being broken. In particular, it is desirable to arrange the puncturing members 31 so that the puncturing members 31 can be substantially perpendicular to the unfolded branch portions 10b.

Furthermore, it is desirable to increase the length of each of the puncturing members 11 and 31 and/or the inclination angle with respect to the surface of the living tissue 20 as the depth to a region to which the medical agent 14 is to be injected increases. For example, when the surface layer 21 is thick or when the living tissue 20 is to be punctured deeply, it is preferable to increase the lengths of the puncturing members 11 and 31 and/or to increase the inclination angle with respect to the surface of the living tissue 20.

Moreover, each branch portion 10b of the pressing member 10 may be formed by connecting two rigid members to each other with a joint in a foldable manner or may be formed of an elastic member.

Figure 7A:
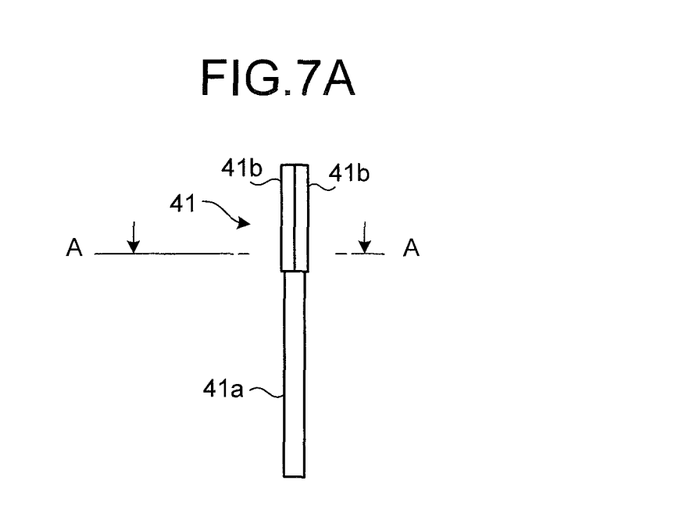
FIG. 7A is a schematic diagram illustrating a modification of the pressing member of the capsule medical apparatus according to the present invention.
Figure 7B:
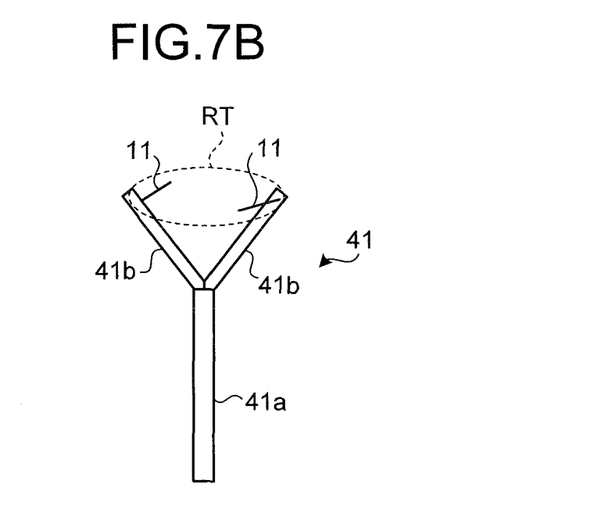
FIG. 7B is another schematic diagram illustrating the modification of the pressing member illustrated in FIG. 7A.
Figure 8A:
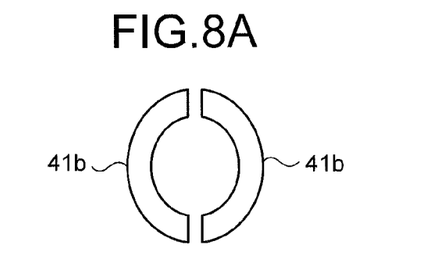
FIG. 8A is a cross-sectional view of a modification of branch portions of the pressing member illustrated in FIG. 7A.
Figure 8B:
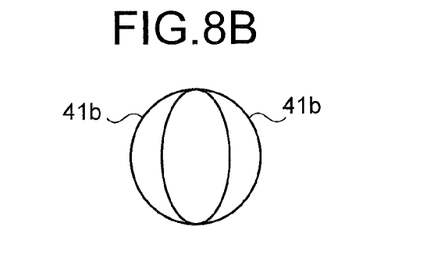
FIG. 8B is a cross-sectional view of another modification of the branch portions of the pressing member illustrated in FIG. 7A.
Figure 8C:
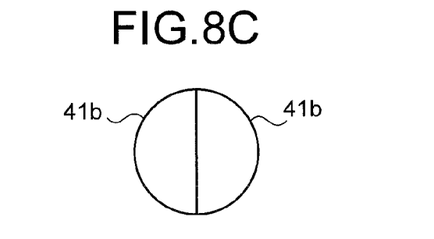
FIG. 8C is a cross-sectional view of still another modification of the branch portions of the pressing member illustrated in FIG. 7A.
Figure 8D:
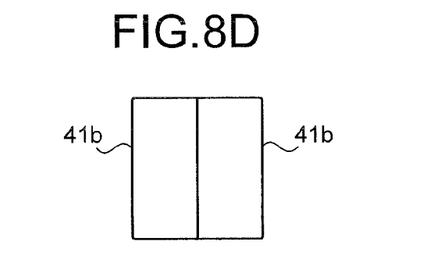
FIG. 8D is a cross-sectional view of still another modification of the branch portions of the pressing member illustrated in FIG. 7A.
Figure 8E:
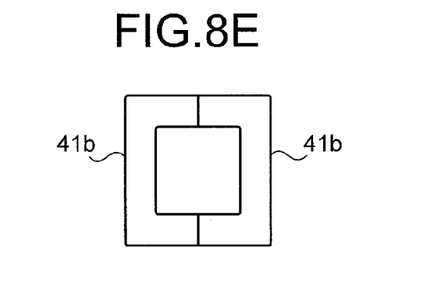
FIG. 8E is a cross-sectional view of still another modification of the branch portions of the pressing member illustrated in FIG. 7A.

Various modifications of the pressing member may be made. For example, as in a pressing member 41 illustrated in FIG. 7A and FIG. 7B, two non-bendable branch portions 41b and 41b may be formed of linear members so as to be spread apart at a base portion 41a in a radially outward direction toward the pressing direction, i.e., may be formed of the linear members of which end portions can be spread apart in the radial direction of the rotation axis so as to form a cone shape. In this case, the branch portions 41b are spread apart directly at the base portion 41a in the radially outward direction of the base portion 41a.

In this case, the cross-sections of the branch portions 41b and 41b may be in various shapes as illustrated in FIG. 8A to FIG. 8E, such as a C-shape, a crescent shape, a semilunar shape, a rectangular shape, or a U-shape. Each of FIG. 8A to FIG. 8E is a cross-sectional view of the cross section taken along A-A of FIG. 7A.

Figure 9:
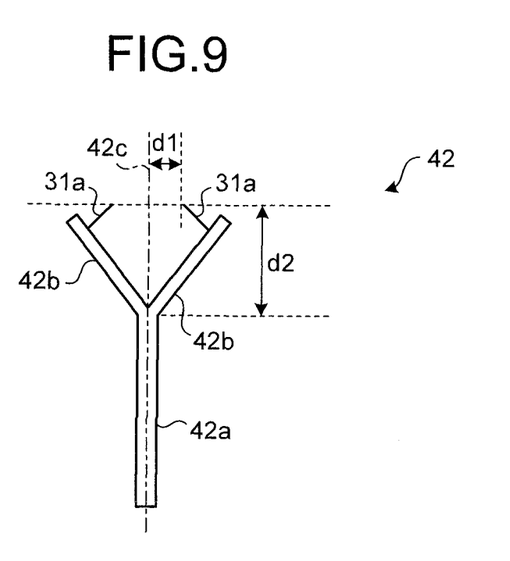
FIG. 9 is a schematic diagram illustrating an example of arrangement of the puncturing members in the capsule medical apparatus according to the present invention.

As illustrated in FIG. 9, it is desirable to arrange such that, when branch portions 42b of a pressing member 42 are spread apart from each other, the end of each puncturing member 31a is at a position shifted by an arbitrary distance d1 from a central axis 42c of a base portion 42a in a direction in which the branch portions 42b spread apart and a distance d2 from the end of the base portion 42a to the end of each puncturing member 31a in the direction of the central axis 42c becomes the farthest than the other components.

Figure 10:
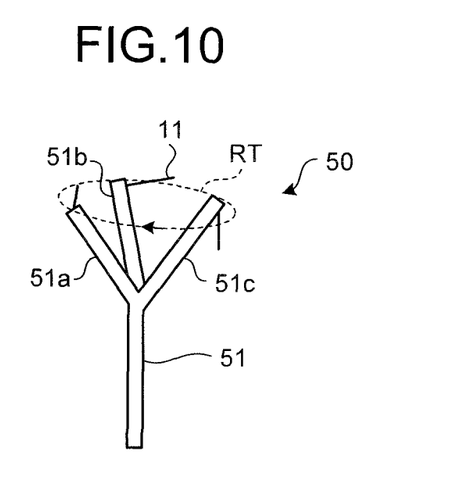
FIG. 10 is a schematic diagram illustrating a modification of the pressing member of the capsule medical apparatus according to the present invention.
Figure 11:
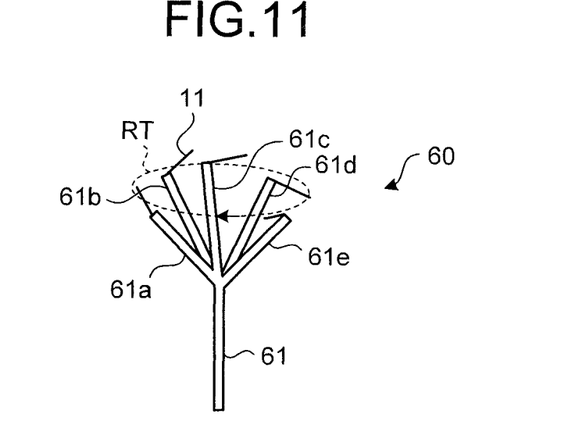
FIG. 11 is a schematic diagram illustrating another modification of the pressing member of the capsule medical apparatus according to the present invention.
Figure 12:
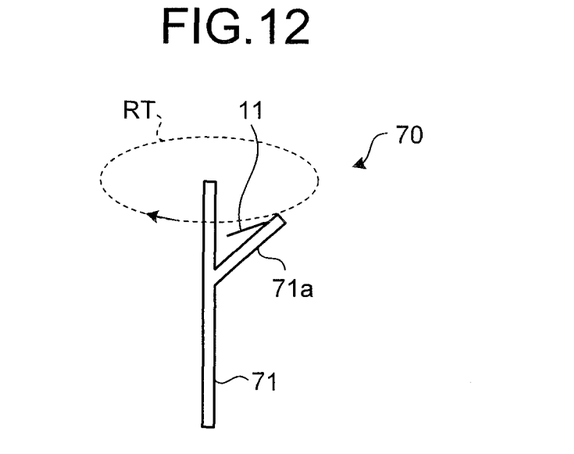
FIG. 12 is a schematic diagram illustrating still another modification of the pressing member of the capsule medical apparatus according to the present invention.

Furthermore, the branch portions are not limited to two, and three or more branch portions may be arranged. For example, a pressing member 50 illustrated in FIG. 10 has three branch portions 51a to 51c on the end side of a base portion 51, and a pressing member 60 illustrated in FIG. 11 has five branch portions 61a to 61e on the end side of a base portion 61. Furthermore, it is possible to mount the puncturing members 11 on all of the branch portions or to mount the puncturing members 11 on only desired branch portions. Moreover, a branch portion may be formed as a branch portion 71a of a pressing member 70 as illustrated in FIG. 12 by bifurcating a base portion 71 into a branch in the middle of the base portion 71.

Figure 13:
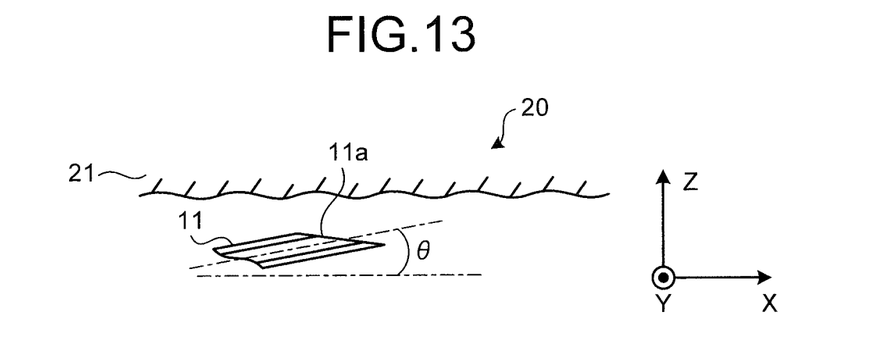
FIG. 13 is a schematic diagram illustrating a modification of arrangement of the puncturing members in the capsule medical apparatus according to the present invention.
Figure 14:
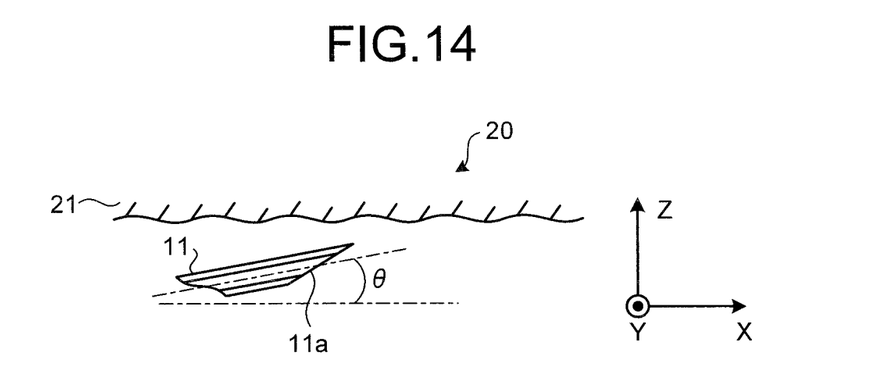
FIG. 14 is a schematic diagram illustrating another modification of the arrangement of the puncturing members in the capsule medical apparatus according to the present invention.

The discharge port of each puncturing member 11 is generally cut diagonally. Therefore, it is possible to mount the puncturing members 11 diagonally so that a discharge port 11a faces the surface layer 21 side of the living tissue 20 as illustrated in FIG. 13, or it is possible to mount the puncturing members 11 diagonally so that the discharge port 11a faces the opposite side of the surface layer 21 side of the living tissue 20 as illustrated in FIG. 14. In the example illustrated in FIG. 13, there is an advantage in that the medical agent is less likely to leak after the puncture. In the example illustrated in FIG. 14, there is an advantage in that the living tissue 20 can more reliably be punctured. In FIG. 13 and FIG. 14, the inclination angle of the puncturing members 11 with respect to the plane substantially perpendicular to the rotation axis of the pressing member is represented by θ.

Figure 15A:
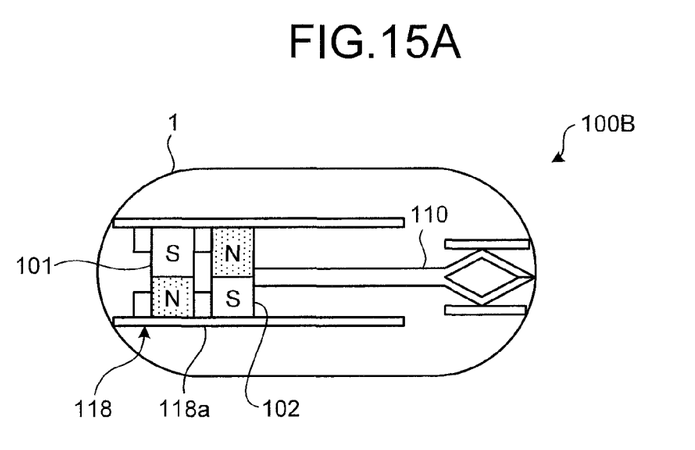
FIG. 15A is a schematic diagram illustrating a modification of an actuator of the capsule medical apparatus according to the present invention.

Although the actuator 18 is not particularly explained in the embodiment described above, the actuator 18 may be formed of a motor or the like. Furthermore, as in a capsule medical apparatus 100B illustrated in FIG. 15A and FIG. 15B, it is possible to use a magnetic actuator 118. In the magnetic actuator 118, discoid permanent magnets 101 and 102 are disposed on the opposite side of a pressing member 110 inside a cylinder 118a. The permanent magnet 101 is fixedly disposed in the cylinder 118a at the end side in the radial direction, while the permanent magnet 102 supports the pressing member 110 and is inserted to be disposed in the cylinder 118a so as to be magnetically coupled to the permanent magnet 101 before the process of injecting a medical agent is performed (see FIG. 15A). Thereafter, when a magnetic field B for inverting the permanent magnet 102 is applied from the outside, the permanent magnet 102 rotates in a direction indicated by an arrow D3 and is displaced to the living tissue 20 side as indicated by a white arrow D4 due to the repelling force by the polarity of the permanent magnet 101, so that the pressing member 110 protrudes toward the living tissue 20 side (see FIG. 15B).

Figure 15B:
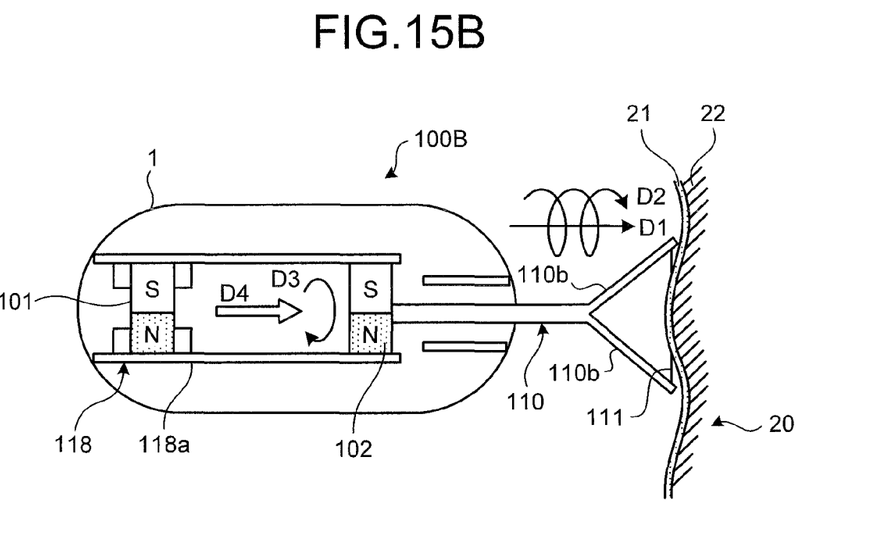
FIG. 15B is another schematic diagram illustrating the modification of the actuator illustrated in FIG. 15A.

Each branch portion 110b of the pressing member 110 is unfolded from a folded state and twists the surface layer 21 of the living tissue 20, so that each puncturing member 111 punctures the surface layer 21 and the medical agent is injected.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A capsule medical apparatus comprising:
    a casing;
    a pressing member configured to contact and press a surface of a living tissue;
    a driving unit that causes the pressing member to protrude from the casing and to press the surface of the living tissue while rotating the pressing member around a rotation axis parallel to a direction in which the pressing member protrudes; and
    a needle-like puncturing member that is arranged on the pressing member and punctures the living tissue in an oblique direction with respect to the surface of the living tissue to thereby inject a medical agent into the living tissue along with the rotation of the pressing member driven by the driving unit, wherein the pressing member is formed of linear members, has an end portion spreadable in a radial direction of the rotation axis, is foldable to be in a state in which the end portion is not spread, is stored in the casing in a folded manner, is configured to be unfolded when protruding to an outside of the casing and be stored in the casing in the folded manner after the medical agent is injected, wherein the puncturing member is arranged on the pressing member at a distance away from an end of the pressing member that presses the surface of the living tissue.

2. The capsule medical apparatus according to claim 1, wherein
    the puncturing member is arranged in a plane substantially perpendicular to the rotation axis of the pressing member, and
    a puncture direction of the puncturing member corresponds to a direction in which the puncturing member comes into contact with a rotational trajectory in a vicinity of an end of the pressing member.

3. The capsule medical apparatus according to claim 1, wherein
    a base portion of the puncturing member is at a position shifted by a predetermined distance from an end of the pressing member toward a base end side of the pressing member, and an end of the puncturing member is at a more forward position than the base portion of the puncturing member in a protruding direction of the pressing member when the pressing member protrudes.

4. The capsule medical apparatus according to claim 1, wherein
    at least one of a length of the puncturing member and an inclination angle with respect to the surface of the living tissue is increased as a depth from the surface of the living tissue to a region to which a medical agent is to be injected increases.

5. The capsule medical apparatus according to claim 1, wherein
    the pressing member is formed of the linear members of which end portions are spreadable in the radial direction of the rotation axis so as to form a cone shape.

6. The capsule medical apparatus according to claim 1, wherein
    after the puncturing member injects the medical agent, the driving unit rotates the pressing member around the rotation axis in a direction opposite to a direction in which the pressing member rotates before the medical agent is injected, to thereby move the pressing member away from the surface of the living tissue.

7. The capsule medical apparatus according to claim 1, further comprising a magnetic body arranged inside the casing.

8. The capsule medical apparatus according to claim 1, wherein the driving unit includes a driving magnetic body, and causes the pressing member to rotate and be pressed against the surface of the living tissue by rotating the driving magnetic body by an induction field applied from the outside.

9. The capsule medical apparatus according to claim 1, further comprising an imaging unit and an illuminating unit.

\* \* \* \* \*